(12) United States Patent
Dias

(10) Patent No.: US 12,642,468 B2
(45) Date of Patent: Jun. 2, 2026

(54) HEART RATE MEASUREMENT AND MENTAL STATE DETECTION SYSTEM AND METHOD FOR MEASURING HEART INTERBEAT INTERVAL AND DETECTING A DIRECTION OF ATTENTION OF AN INDIVIDUAL ENGAGED IN AN ACTIVITY

(71) Applicant: Andrea Carvalho Dias, Kapolei, HI (US)

(72) Inventor: Andrea Carvalho Dias, Kapolei, HI (US)

(73) Assignee: ACTION SPORT PSYCH, Honolulu, HI (US)

( * ) Notice: Subject to any disclaimer, the term of this patent is extended or adjusted under 35 U.S.C. 154(b) by 0 days.

(21) Appl. No.: 18/749,638

(22) Filed: Jun. 21, 2024

(65) Prior Publication Data

US 2024/0423522 A1     Dec. 26, 2024

Related U.S. Application Data

(60) Provisional application No. 63/522,408, filed on Jun. 21, 2023.

(51) Int. Cl.
| | |
|---|---|
| *A61B 5/16* | (2006.01) |
| *A61B 5/00* | (2006.01) |
| *A61B 5/024* | (2006.01) |
| *G16H 15/00* | (2018.01) |

(52) U.S. Cl.
CPC ............ *A61B 5/168* (2013.01); *A61B 5/0022* (2013.01); *A61B 5/0077* (2013.01); *A61B 5/02405* (2013.01); *A61B 5/02438* (2013.01); *A61B 5/742* (2013.01); *G16H 15/00* (2018.01)

(58) Field of Classification Search
CPC ..... A61B 5/168; A61B 5/0022; A61B 5/0077; A61B 5/02405; A61B 5/02438; A61B 5/742
USPC .......................................................... 600/301
See application file for complete search history.

(56) References Cited

U.S. PATENT DOCUMENTS

| | | | | |
|---|---|---|---|---|
| 11,039,763 | B2 * | 6/2021 | Ye .......................... | A61B 5/1118 |
| 11,167,172 | B1 * | 11/2021 | Putnam ................ | A61B 5/7275 |
| 2008/0214903 | A1 * | 9/2008 | Orbach .................... | A61B 5/33 705/2 |
| 2012/0084054 | A1 * | 4/2012 | Yuen .................... | A61B 5/0004 702/160 |
| 2015/0273313 | A1 * | 10/2015 | Chen .................... | A61B 5/4866 700/91 |
| 2016/0066835 | A1 * | 3/2016 | He ...................... | A63B 24/0087 482/4 |
| 2016/0100787 | A1 * | 4/2016 | Leung .................... | A61B 5/165 600/490 |
| 2016/0338640 | A1 * | 11/2016 | Chan ...................... | A61B 5/352 |

(Continued)

*Primary Examiner* — Michael J Lau
(74) *Attorney, Agent, or Firm* — Plager Schack LLP; Mark H. Plager; Stephen Hallberg

(57)     ABSTRACT

A heart rate measurement and mental state detection system and a heart rate measurement and mental state detection method for measuring heart interbeat interval and detecting a direction of attention of an individual engaged in an activity are disclosed. The heart rate measurement and mental state detection and method are configured to instantaneously detect and measure focused attention of an individual during a pre-action phase before the individual performs an action involved in an activity while the individual engages in the activity.

11 Claims, 7 Drawing Sheets

(56)     References Cited

U.S. PATENT DOCUMENTS

| | | | | |
|---|---|---|---|---|
| 2017/0281080 A1* | 10/2017 | Chuang | ................ | A61B 5/7253 |
| 2021/0005224 A1* | 1/2021 | Rothschild | ........... | H04N 9/8205 |
| 2021/0008413 A1* | 1/2021 | Asikainen | ............ | G06F 3/0304 |
| 2021/0077031 A1* | 3/2021 | Fukunaga | ............... | G06F 3/015 |
| 2021/0255826 A1* | 8/2021 | Devine | ................ | H04W 12/55 |
| 2022/0133194 A1* | 5/2022 | Bach | .................... | A61B 5/6801 |
| | | | | 600/544 |
| 2022/0240790 A1* | 8/2022 | Smit | ................... | A61B 5/1135 |
| 2022/0370853 A1* | 11/2022 | Henderson | ......... | A41D 13/0015 |
| 2023/0039903 A1* | 2/2023 | Brammer | .............. | A61B 5/681 |
| 2023/0177947 A1* | 6/2023 | Fry | ...................... | G08B 25/016 |
| | | | | 340/573.1 |

* cited by examiner

HEART RATE MEASUREMENT AND MENTAL STATE DETECTION SYSTEM AND METHOD FOR MEASURING HEART INTERBEAT INTERVAL AND DETECTING A DIRECTION OF ATTENTION OF AN INDIVIDUAL ENGAGED IN AN ACTIVITY

This application claims benefit to U.S. Provisional Patent Application 63/522,408, entitled "A HEART RATE DECELERATION SYSTEM AND METHOD FOR MEASURING MENTAL STATES AND PREDICTING ATHLETIC PERFORMANCE OF ATHLETES AND OTHER SPORTS PARTICIPANTS BY WAY OF A HEART RATE DECELERATION SPORTS WATCH APP," filed Jun. 21, 2023. The U.S. Provisional Patent Application 63/522,408 is incorporated herein by reference.

BACKGROUND

Embodiments of the invention described in this specification relate generally to sports and fitness apps, and more particularly, to a heart rate measurement and mental state detection system and a heart rate measurement and mental state detection method for measuring heart interbeat interval and detecting a direction of attention of an individual engaged in an activity.

From ancient civilizations to the Greek philosopher Aristotle, the heart has been associated as the seat of the emotions. Today, this sentiment predominates in cultural references almost everywhere. For instance, the heart as the emotional center of the individual is often shown in children's cartoons, where characters often exhibit hearts dramatically blowing out of their chests when experiencing fear or love. As such, most people develop an intuitive sense that emotional well-being can be found in the heart.

This underscores the current understanding of the mind and body as one unified system. In the current understanding, the mind is not a separate entity working apart from the body. When the individual is engaged in multiple behaviors, the psychological activities are translated into multiple physiological processes. Psychophysiology is the science that uses specialized instruments to measure physiological parameters and translate the mental processes that individuals are unaware of By making individuals aware of the processes, they can re-train new responses and enhance performance.

However, it was not until about the late 1960s and early 1970s that researchers began investigating the relationship between heart rate and psychological phenomena. Among the various research was an investigation of the relationship between focused attention and heart rate deceleration. Today, after more than fifty years of studies investigating attention, heart rate, and performance, Heart Rate Deceleration (HRD) and Heart Rate Acceleration (HRA) during a pre-action phase of self-paced sports became recognized as biomarkers of focused attention (that is, focused attention to the task at hand, whatever aspect of the self-paced sport being engaged by the individual). The pre-action phase for self-paced sports and activities is approximately the six seconds prior to the individual performing the action. In particular, pre-action focused attention typically precedes better performance by the individual for the task at hand. For example, if, during the pre-action, the individual's mind jumps to the future to worry about the consequences of a bad performance or moves to the past to associate the current situation with a previous defeat or instance of under-performance, the individual's heart rate will accelerate, which can be measured (HRA biomarker). Consequently, the individual's ability to perform the task at hand decreases.

Heart rate monitors are readily available in the market and give feedback on an individual's heart rate. Furthermore, there are several existing sports and fitness devices, apps, and other software that can measure athletic performance (such as speed, strength, etc.), and things like body state and vitals in real time, but fail to translate it to any measurable aspect pertaining to attention, focused attention, mental states, etc. In behavioral sciences, so many things are interdependent or depend on a series of other factors. As such, the measures obtained by heart rate monitors, sports and fitness devices, apps, and other software must be interpreted by a sport psychophysiologist or sport psychology professional.

Currently, none of the existing devices/apps utilize HRA and/or HRD as measures of focused attention in the realm of athletics performance, despite the existing technology devices, apps, software, and so on. In particular, none of the existing options are configured to validate HRD (deceleration) as a measure of focused attention that predicts better performance and/or to validate HRA (acceleration) as a measure of unfocused attention that predicts sub-optimal performance in the realm of athletics performance or performance of any task (whether athletic or not) that involves focused attention.

Therefore, what is needed is a way to provide a measure of focused attention, as a predictor of better performance, during the pre-action phase of self-paced sports, athletics, fitness activities, other activities, or tasks that benefit from focused attention, based on HRD and HRA and preferably, a way to measure HRD and HRA instantaneously, during the pre-action phase just before the action, compare the heart rate measurements to actual performance of the task at hand, and give feedback to coaches and athletes right after their performance.

BRIEF DESCRIPTION

A novel heart rate measurement and mental state detection system is disclosed which is configured to instantaneously detect and measure focused attention of an individual during a pre-action phase before the individual performs an action. In some embodiments, the heart rate measurement and mental state detection system comprises a heart rate monitor, a camera, a computing device, and a sport psychophysiology-validated heart rate monitoring software application. In some embodiments, the heart rate measurement and mental state detection system further comprises a smart watch that is paired to the heart rate monitor. In some embodiments, the heart rate measurement and mental state detection system further comprises one or more wireless data communication devices. In some embodiments, the wireless data communication devices comprise at least one of a Bluetooth module and a radio-frequency (RF) module. In some embodiments, the RF module comprises one of an ANT+ RF module and a Gymlink module. In some embodiments, an embedded wireless communication device is embedded as a component of the heart rate monitor. In some embodiments, a wireless communication device is incorporated into a communications unit of the smart watch. In some embodiments, an integrated wireless communication device is integrated into the computing device. In some embodiments, an external wireless communication device is attached the computing device. In some embodiments, a wireless camera communication device is provided as a component of the camera.

In some embodiments, the heart rate monitor is configured to capture heart rate data during performance of an activity and provide the heart rate data to either the computing device or the smart watch. In some embodiments, the heart rate data is provided to the computing device by the heart rate monitor in real-time as the heart rate data is being captured during performance of the activity. In some embodiments, the heart rate data is provided by the heart rate monitor to the smart watch instantaneously and the smart watch, in turn, provides the heart rate data to the computing device in real-time during performance of the activity.

In some embodiments, the camera is configured to capture imagery during performance of the activity and provide the imagery to the computing device. In some embodiments, the imagery captured during performance of the activity comprises a plurality of still frame images captured at a plurality of moments while the individual is performing the activity. In some embodiments, the camera comprises a video camera and the imagery captured during performance of the activity comprises a video of an individual performing the activity. In some embodiments, the video camera is configured to transmit the video to the computing device in real-time as the video is being captured during performance of the activity.

In some embodiments, the computing device comprises at least one of a laptop computer and a tablet computing device. In some embodiments, the sport psychophysiology-validated heart rate monitoring software application is installed on the computing device and, when running on a processing unit of the computing device, is configured to receive the heart rate data and the imagery captured by the camera during performance of the activity. In some embodiments, the sport psychophysiology-validated heart rate monitoring software application is further configured to analyze and validate the heart rate data. In some embodiments, the sport psychophysiology-validated heart rate monitoring software application is further configured to synchronize a timeline of the imagery with a timeline of the heart rate data. In some embodiments, In some embodiments, the sport psychophysiology-validated heart rate monitoring software application is further configured to visually output the timeline-synchronized imagery and heart rate data for viewing on a screen of the computing device.

Also disclosed in this specification is novel heart rate measurement and mental state detection method for measuring heart interbeat interval and detecting a direction of attention of an individual engaged in an activity. In some embodiments, the heart rate measurement and mental state detection method for measuring heart interbeat interval and detecting a direction of attention of an individual engaged in an activity comprises (i) wearing, by an individual, a heart rate monitor applied approximately to a chest area of the individual while the individual engages in performance of an activity, (ii) connecting a camera to a computing device with a sport psychophysiology-validated heart rate monitoring software application installed, (iii) simultaneously starting the heart rate monitor and the camera to capture, at a simultaneous start time, a sequence of heart rate data of the individual and a sequence of images (video) of the individual during performance of the activity, (iv) capturing, by the heart rate monitor, heart rate data during performance of the activity by the individual, (v) receiving, by the computing device, the heart interbeat interval data of the heart rate data captured by the heart rate monitor, (vi) analyzing and validating, by the sport psychophysiology-validated heart rate monitoring software application, the heart interbeat interval data, (vii) capturing, by the camera contemporaneously with the heart rate monitor capturing the heart rate data, video of the individual during performance of the activity, (viii) receiving, by the computing device, the video captured by the camera, (ix) pairing, by the sport psychophysiology-validated heart rate monitoring software application, the sequence of heart rate data with the video, (x) synchronizing, by the sport psychophysiology-validated heart rate monitoring software application, a heart rate data timeline of the sequence of heart rate data with a video timeline of the video starting at the simultaneous start time, and (xi) visually outputting, on a screen of the computing device by the sport psychophysiology-validated heart rate monitoring software application, the time-synchronized video and heart rate data for playback viewing by a user operating the computing device. In some embodiments, the user viewing the time-synchronized heart rate data and video is the individual who performed the activity. In some embodiments, the user viewing the time-synchronized heart rate data and video is a coach of the individual who performed the activity. In some embodiments, the user viewing the time-synchronized heart rate data and video is a specialist in sport psychophysiology who is able to interpret the data in view of the demands of the activity performed by the individual.

In some embodiments, the heart rate measurement and mental state detection method further comprises adding event markers to the heart rate data as the video is being viewed by the user. In some embodiments, the event markers comprise one or more of a pre-action event marker, an action event marker, a sport demand event marker, a neutral time event marker, a no go event marker, a downtime event marker, and a custom event marker.

In some embodiments, the heart rate measurement and mental state detection method further comprises delimiting time segments of the heart rate data timeline based on the event markers added to the heart rate data. In some embodiments, the heart rate measurement and mental state detection method further comprises calculating heart rate variability (HRV) data based on changes between the delimited time segments. In some embodiments, calculating HRV comprises analyzing heart rate deceleration (HRD) data. In some embodiments, calculating HRV comprises analyzing heart rate acceleration (HRA) data. In some embodiments, calculating HRV comprises analyzing standard deviation of NN (SDNN) data. In some embodiments, calculating HRV comprises analyzing root mean square of the successive differences (RMSSD) data. In some embodiments, calculating HRV comprises analyzing a ratio of low-frequency power divided by high-frequency power (LH/HF ratio).

In some embodiments, the heart rate measurement and mental state detection method further comprises adding the neutral time event marker to a particular time segment of the heart rate data timeline spanning a video timeline segment spanning a first video timeline position at a moment of completion of a first activity and a second video timeline position at a moment of starting performance of a second activity.

In some embodiments, the heart rate measurement and mental state detection method further comprises visually outputting a pop-up box through which the user viewing the time-synchronized heart rate data and video can evaluate the outcome of the performance of the activity and mark the performance of the activity with an activity performance outcome designation. In some embodiments, the activity performance outcome designation is selected by the user from a plurality of activity performance outcome designations. In some embodiments, the plurality of activity performance outcome designations comprise a good performance designation, a regular performance designation, a mistake designation, and a nothing designation. In some embodiments, the activity performance outcome designation is entered as free-form text input by the user.

In some embodiments, the heart rate measurement and mental state detection method further comprises visually outputting a report writing interface tool which, when selected by the user, generates a report of the performance of the activity with respect to one or more calculated parameters comprising the HRV data, the HRD data, the HRA data, the SDNN data, the RMSSD data, and the LH/HF ratio.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having thus described the invention in general terms, reference is now made to the accompanying drawings, which are not necessarily drawn to scale, and which show different views of different example embodiments.

Figure 1:
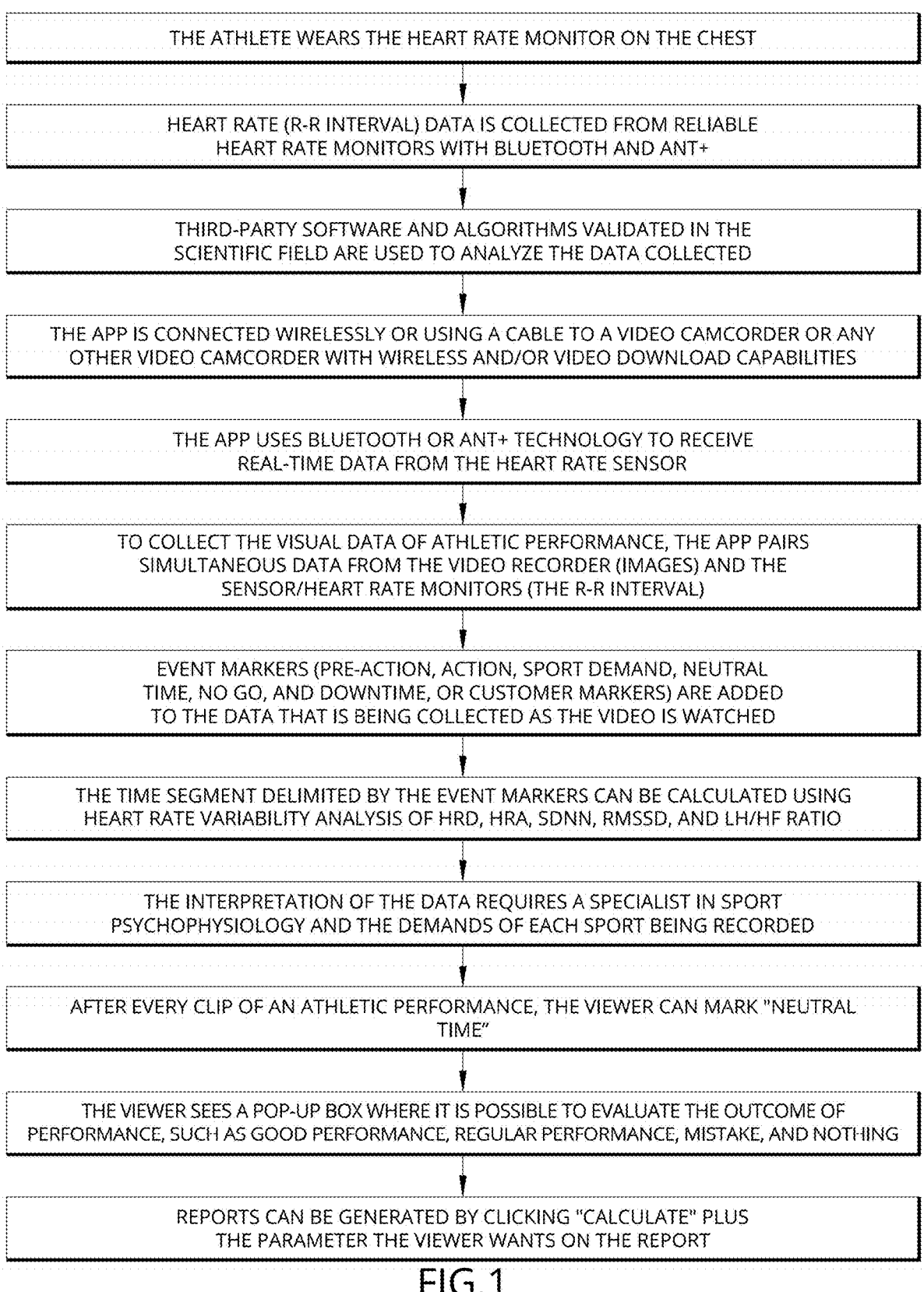

FIG. 1 conceptually illustrates a heart rate measurement and mental state detection method for measuring heart interbeat interval and detecting a direction of attention of an individual engaged in an activity in some embodiments.

Figure 2:
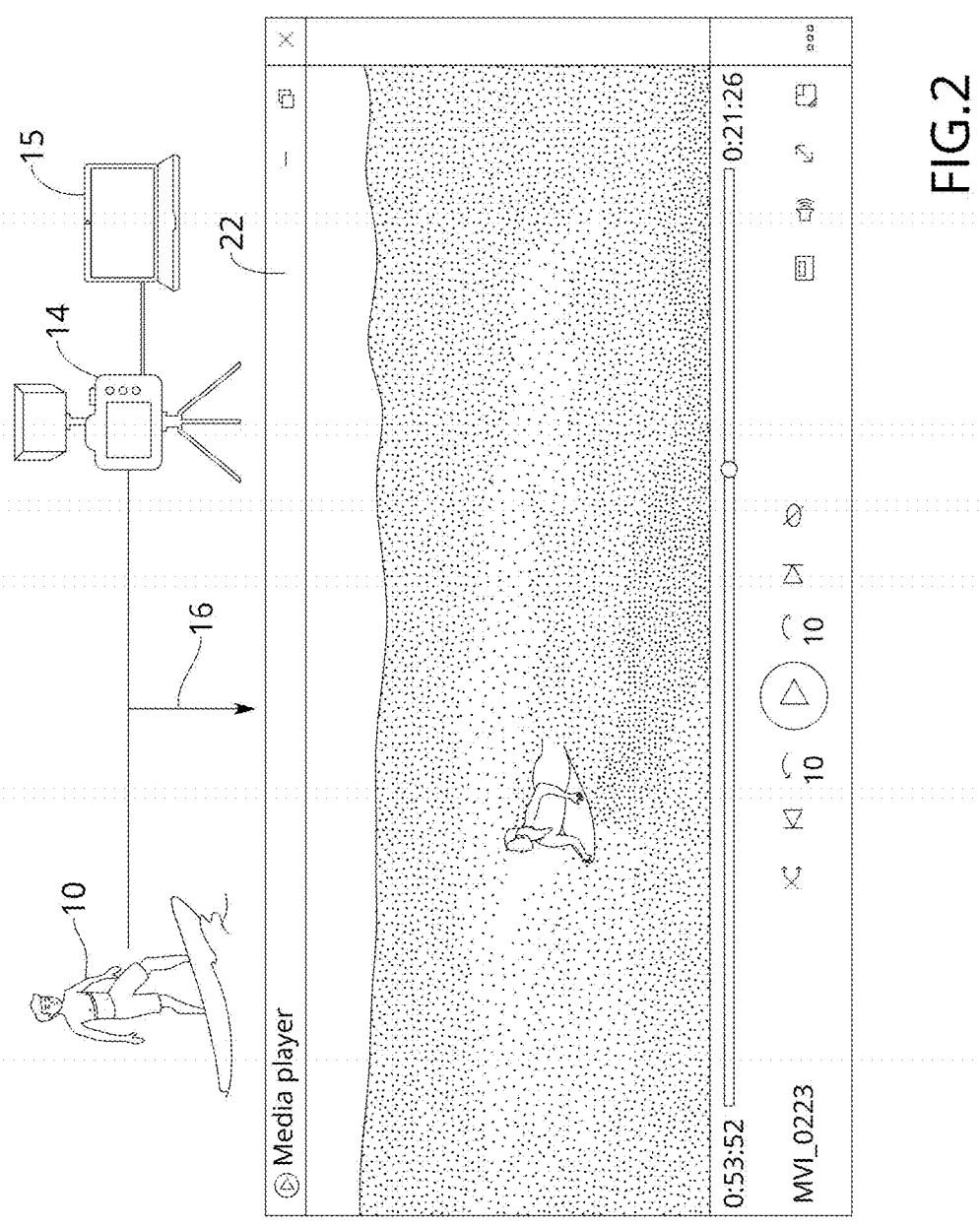

FIG. 2 conceptually illustrates a heart rate measurement and mental state detection system in some embodiments that configured to capture a video of an individual engaging in an activity and capture heart rate data of the individual to instantaneously detect and measure focused attention of the individual during a pre-action phase and as the individual performs the activity.

Figure 3:
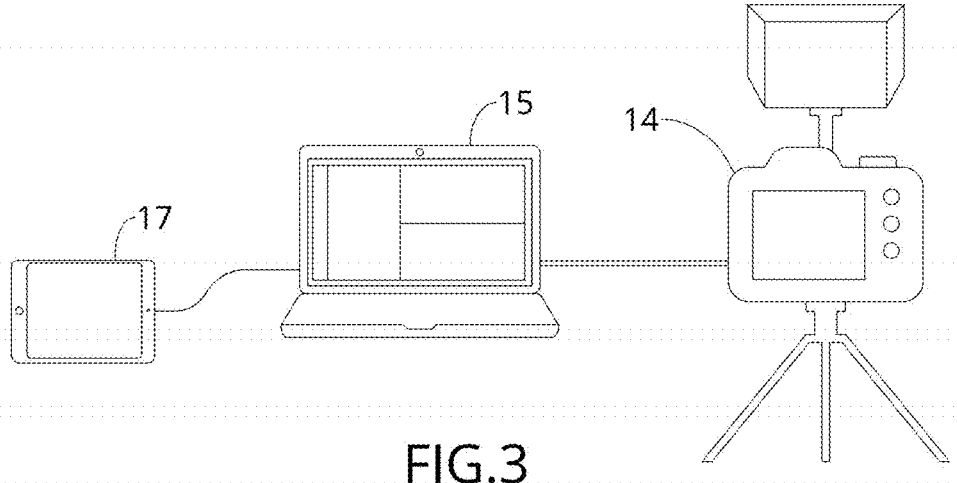

FIG. 3 conceptually illustrates components of a heart rate measurement and mental state detection system with a camera, a laptop computer, and a tablet computing device in some embodiments.

Figure 4:
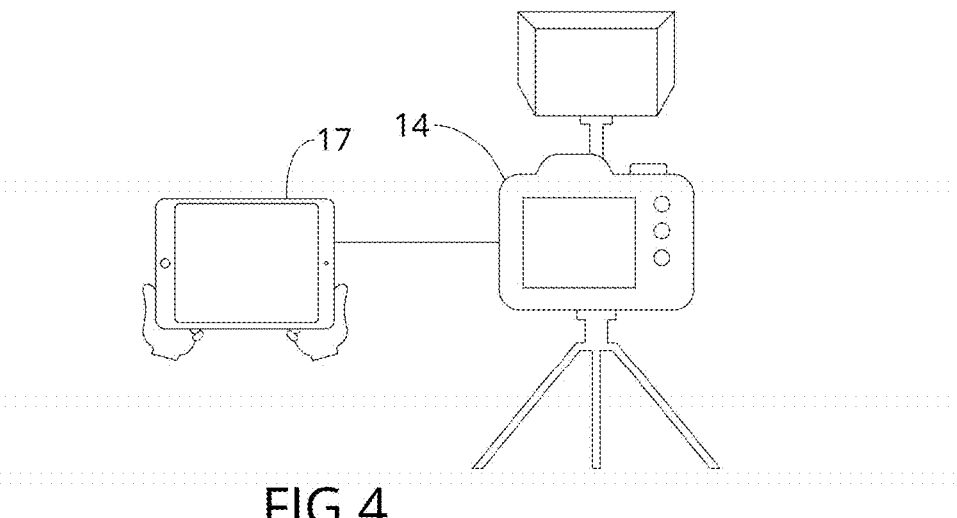

FIG. 4 conceptually illustrates components of a heart rate measurement and mental state detection system with a camera and a tablet computing device in some embodiments while a user is operating the tablet computing device.

Figure 5:
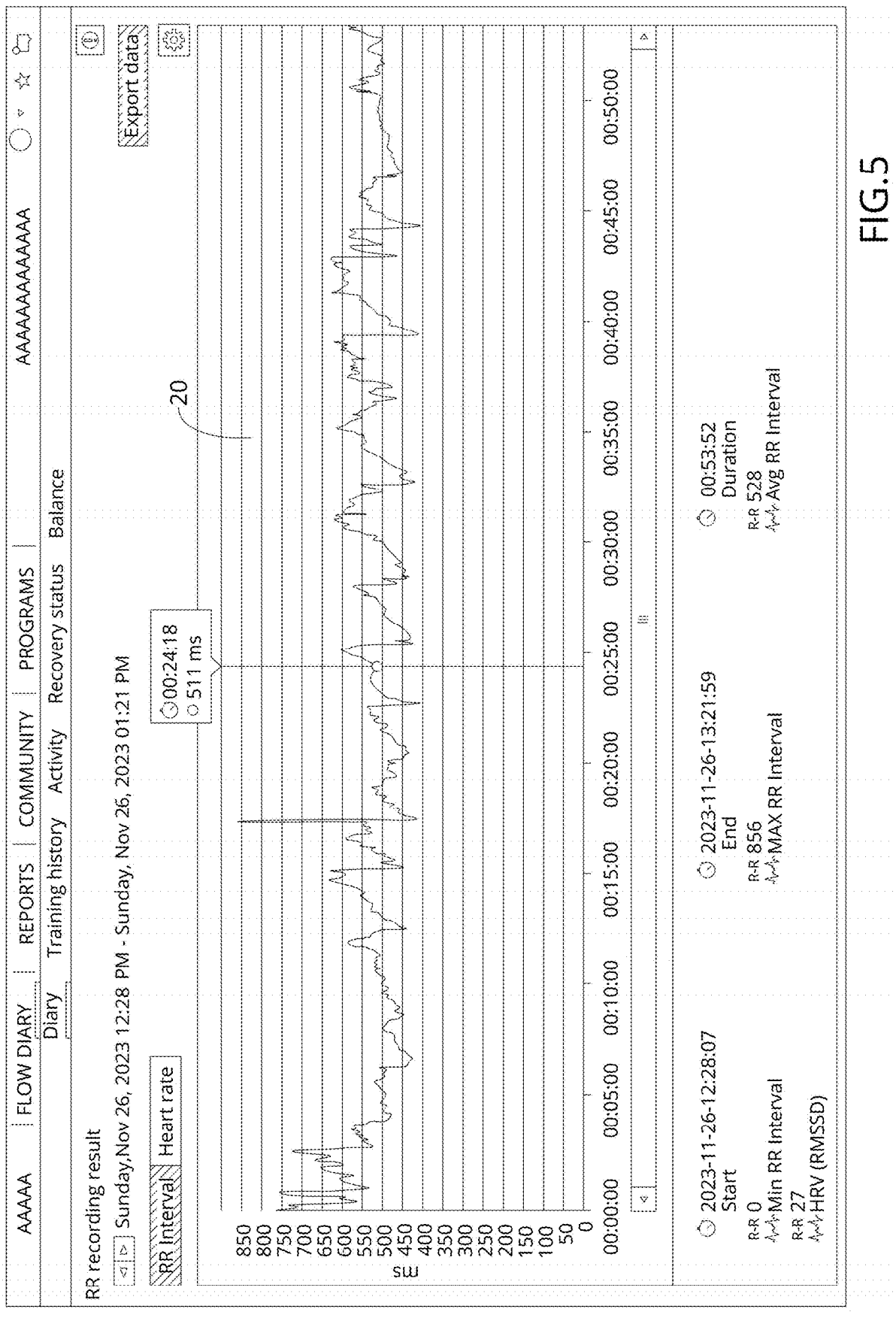

FIG. 5 conceptually illustrates an example view of formatted heart rate data as provided for review in some embodiments of the heart rate measurement and mental state detection system.

Figure 6:
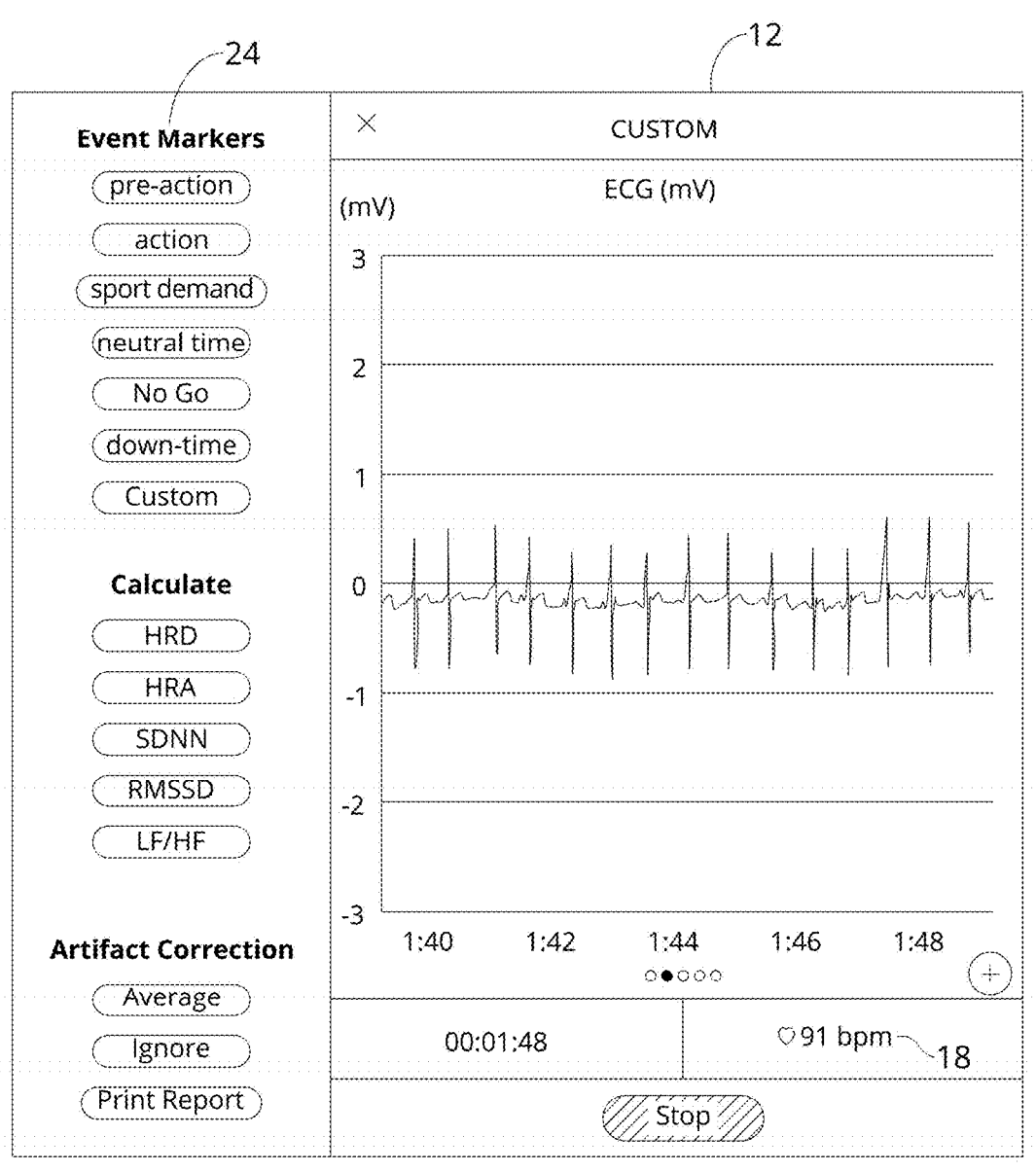

FIG. 6 conceptually illustrates an example view of selective controls and a PQRS heart wave (signal) in some embodiments of the heart rate measurement and mental state detection system which helps a sport psychophysiologist to see artifacts and correct them.

Figure 7:
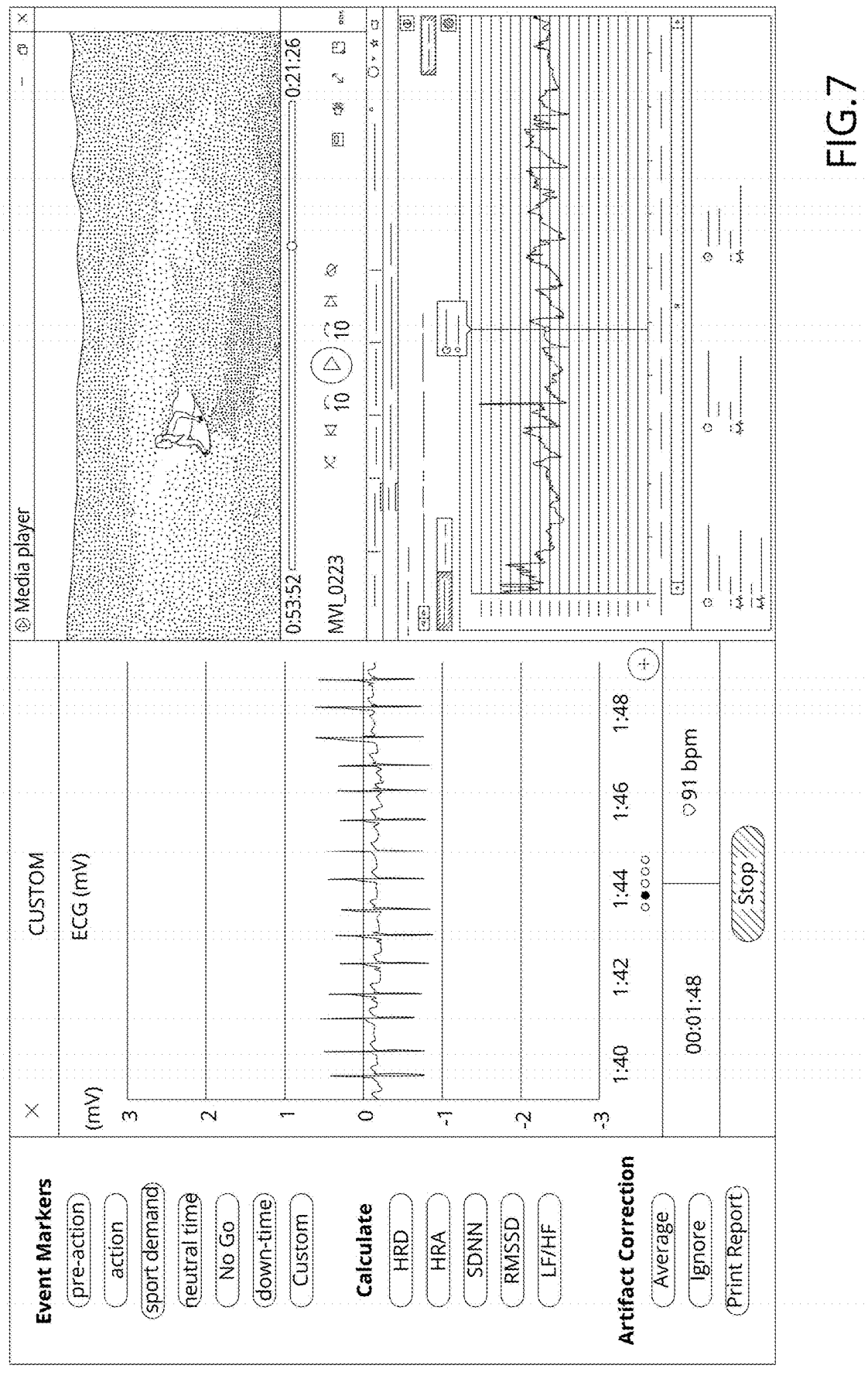

FIG. 7 conceptually illustrates a combined view of the selective controls, the PQRS signal view, a media player for video playback of the captured video, and the formatted heart rate data view with a heart rate data timeline that is synchronized to a video timeline of the captured video shown in the media player.

Figure 8:
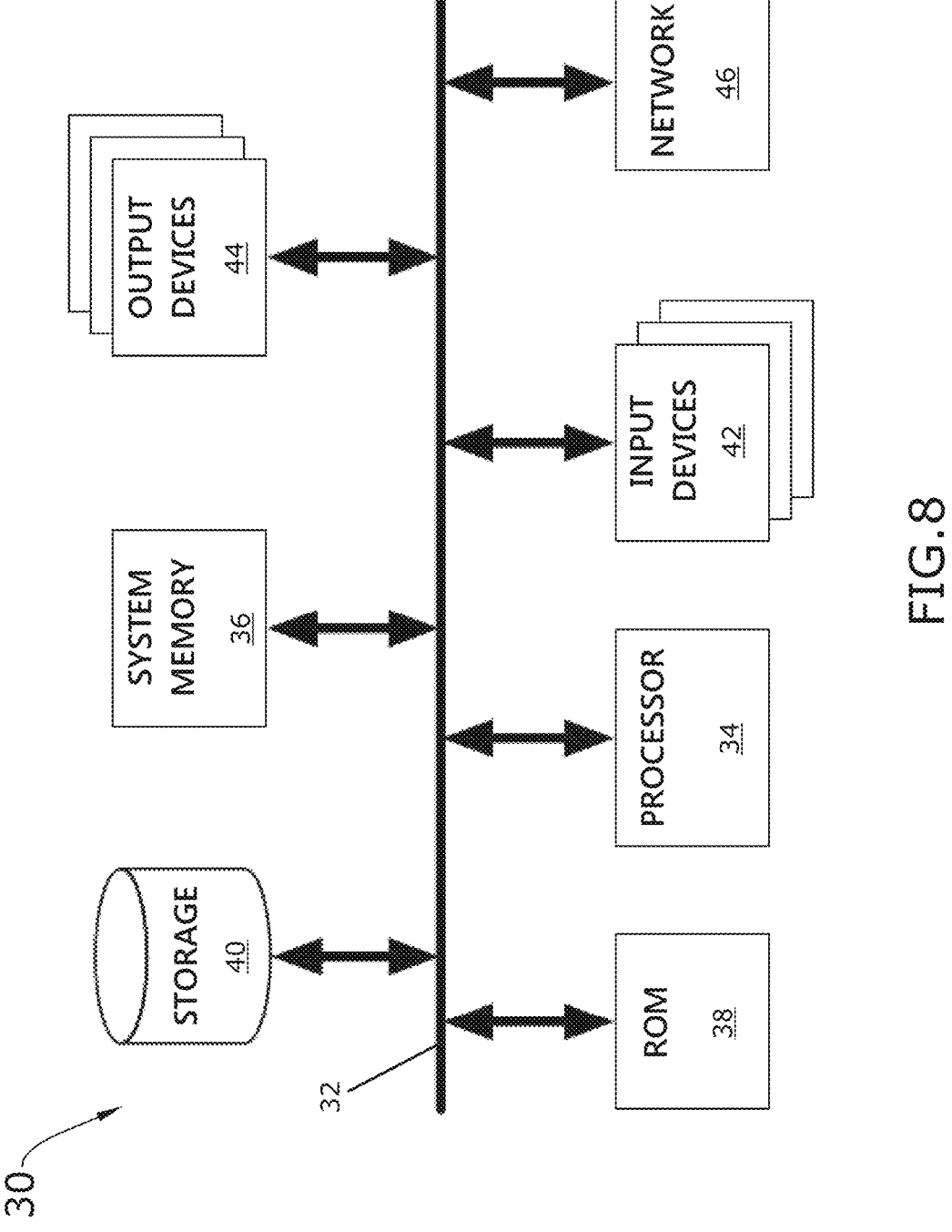

FIG. 8 conceptually illustrates an electronic system with which some embodiments of the invention are implemented.

DETAILED DESCRIPTION

In the following detailed description of the invention, numerous details, examples, and embodiments of the invention are described. Also, several terms are used throughout this description to refer to a direction of attention of an individual, who in preparation to perform the action at hand either directs his or her attention externally or internally. Therefore, in this specification, the terms "selective attention," "focused attention," "focus," "attention," "attentional state," and like terms, mean the direction of attention of the individual, as either externally focused attention, internally focused attention, or a combination of both. In addition, the terms "detect," "detection", "detecting", etc., as used in the specification are intended to mean approximate and/or precise detection, prediction, estimation, and/or other like terms. Furthermore, many of the details described below pertain to fitness-related sports and/or self-paced sports. Also, the terms "instantaneous" and "instantaneously" are used in this specification broadly to mean immediately, real-time (in real-time), near real-time, contemporaneously, soon, and other like terms. However, the invention is not limited to applications in only fitness-related sports and/or self-paced sports, but extend to a wide range of activities that involve directed attention by an individual. For instance, chess, test taking, reaction time test taking, or other activities in which decision-making is involved prior to action by an individual. Therefore, it will be clear and apparent to one skilled in the art that the invention is not limited to the embodiments set forth and that the invention can be adapted for any of several applications.

Embodiments of the invention described in this specification provide a heart rate measurement and mental state detection system and a heart rate measurement and mental state detection method for measuring heart interbeat interval and detecting a direction of attention of an individual engaged in an activity.

In some embodiments, the heart rate measurement and mental state detection system is configured to instantaneously detect and measure a direction of attention of an individual during a pre-action phase before the individual performs an action involved in an activity while the individual engages in the activity. For example, the activity may be baseball, tennis, golf, soccer, basketball, etc., and the athlete in each of those activities is often in a position of following and/or focusing on a target (such target being, for example, a golf ball resting on a tee awaiting the golfer to hit it, a soccer ball and goal for a soccer player performing a penalty kick, a basketball hoop for a basketball player shooting a free throw, etc.). Furthermore, the target can become a repeated focal point in relatively quick succession or may even change while the individual engages in the activity. For instance, the basketball play makes the free throw and now focuses on movement of the basketball by the other team passing between their own players and, eventually, focuses on the tracking the rebound angle of the basketball after a missed shot. Thus, there may be multiple repeated and/or different actions performed by the individual while engaged in the activity. In some embodiments, the heart rate measurement and mental state detection system comprises a heart rate monitor (or heart rate sensor), a camera, a computing device, and a sport psychophysiology-validated heart rate monitoring software application. In some embodiments, the heart rate measurement and mental state detection system further comprises a smart watch that is paired to the heart rate monitor (or sensor). In some embodiments, the heart rate measurement and mental state detection system further comprises one or more wireless data communication devices.

In some embodiments, the heart rate monitor is configured to capture heart rate data during performance of an activity. In some embodiments, the heart rate monitor is further configured to internally store (in a data storage of the heart rate monitor) the heart rate data captured during performance of the activity. In some embodiments, the heart rate monitor is further configured to upload the internally stored heart rate data to the computing device after performance of the activity is completed. In some embodiments, the heart rate monitor is configured to wirelessly transmit the heart rate data captured during performance of the activity. In some embodiments, the heart rate monitor is configured to wirelessly transmit the heart rate data to the smart watch. In some embodiments, the heart rate monitor is configured to wirelessly transmit the heart rate data to the computing device.

In some embodiments, the camera is configured to capture imagery during performance of the activity. In some embodiments, the imagery captured during performance of the activity comprises a video of an individual performing the activity. In some embodiments, the imagery captured during performance of the activity comprises a plurality of still frame images captured at a plurality of moments while the individual is performing the activity. In some embodiments, the camera is further configured to internally store (in a data storage of the camera) the imagery captured during performance of the activity. In some embodiments, the camera is further configured to provide the internally stored imagery to the computing device after performance of the activity is completed and upon connection to the computing device. In some embodiments, the camera is communicably connected to the computing device during performance of the activity. In some embodiments, the camera is configured to transmit the imagery captured during performance of the activity to the computing device. In some embodiments, the camera is further configured to transmit the imagery in real-time as a video stream to the computing device as the imagery is being captured.

In some embodiments, the computing device comprises a laptop computer. In some embodiments, the computing device comprises a personal computer (PC). In some embodiments, the computing device comprises a tablet computing device. In some embodiments, the computing device comprises a smartphone mobile device. In some embodiments, the computing device comprises a single board computer (SBC). In some embodiments, the computing device is communicably connected to the camera. In some embodiments, the computing device is a first computing device and the heart rate measurement and mental state detection system further comprises a second computing device. In some embodiments, the first computing device comprises the laptop computer and the second computing device comprises the tablet computing device. In some embodiments, the first computing device comprises the laptop computer and the second computing device comprises the smartphone mobile device.

In some embodiments, the sport psychophysiology-validated heart rate monitoring software application is installed on the computing device and, when running on a processing unit of the computing device, is configured to receive the heart rate data and the imagery captured during performance of the activity. In some embodiments, the sport psychophysiology-validated heart rate monitoring software application is further configured to analyze and validate the heart rate data. In some embodiments, the sport psychophysiology-validated heart rate monitoring software application is further configured to synchronize a timeline of the imagery with a timeline of the heart rate data. In some embodiments, the sport psychophysiology-validated heart rate monitoring software application is further configured to visually output the timeline-synchronized imagery and heart rate data for playback viewing on a screen of the computing device.

In some embodiments, the smart watch is configured to receive and store heart rate data captured and provided by the heart rate monitor. In some embodiments, the smart watch is configured to connect and upload the stored heart rate data to the computing device.

In some embodiments, the wireless data communication devices comprise a Bluetooth communications module. In some embodiments, the wireless data communication devices comprise a non-Bluetooth radio-frequency (RF) communications device. In some embodiments, the non-Bluetooth RF communications device comprises an ANT+ RF module. In some embodiments, the non-Bluetooth RF communications device comprises a Gymlink module.

In some embodiments, the heart rate measurement and mental state detection method for measuring heart interbeat interval and detecting a direction of attention of an individual engaged in an activity comprises (i) wearing, by an individual, a heart rate monitor applied approximately to a chest area of the individual while the individual engages in performance of an activity, (ii) connecting a camera to a computing device with a sport psychophysiology-validated heart rate monitoring software application installed, (iii) simultaneously starting the heart rate monitor and the camera to capture, at a simultaneous start time, a sequence of heart rate data of the individual and a sequence of images (video) of the individual during performance of the activity, (iv) capturing, by the heart rate monitor, heart rate data during performance of the activity by the individual, (v) receiving, by the computing device, heart interbeat interval data of the heart rate data captured by the heart rate monitor, (vi) analyzing and validating, by the sport psychophysiology-validated heart rate monitoring software application, the heart interbeat interval data, (vii) capturing, by the camera contemporaneously with the heart rate monitor capturing the heart rate data, video of the individual during performance of the activity, (viii) receiving, by the computing device, the video captured by the camera, (ix) pairing, by the sport psychophysiology-validated heart rate monitoring software application, the sequence of heart rate data with the video, (x) synchronizing, by the sport psychophysiology-validated heart rate monitoring software application, a heart rate data timeline of the sequence of heart rate data with a video timeline of the video starting at the simultaneous start time, and (xi) visually outputting, on a screen of the computing device by the sport psychophysiology-validated heart rate monitoring software application, the time-synchronized video and heart rate data for playback viewing by a user operating the computing device. In some embodiments, the user viewing the time-synchronized heart rate data and video is the individual who performed the activity. In some embodiments, the user viewing the time-synchronized heart rate data and video is a coach of the individual who performed the activity. In some embodiments, the user viewing the time-synchronized heart rate data and video is a specialist in sport psychophysiology who is able to interpret the data in view of the demands of the activity performed by the individual.

In some embodiments, the heart rate measurement and mental state detection method further comprises adding event markers to the heart rate data as the video is being viewed by the user. In some embodiments, the event markers comprise one or more of a pre-action event marker, an action event marker, a sport demand event marker, a neutral time event marker, a no go event marker, a downtime event marker, and a custom event marker.

In some embodiments, the heart rate measurement and mental state detection method further comprises delimiting time segments of the heart rate data timeline based on the event markers added to the heart rate data. In some embodiments, the heart rate measurement and mental state detection method further comprises calculating heart rate variability (HRV) data based on changes between the delimited time segments. In some embodiments, calculating HRV comprises analyzing heart rate deceleration (HRD) data. In some embodiments, calculating HRV comprises analyzing heart rate acceleration (HRA) data. In some embodiments, calculating HRV comprises analyzing standard deviation of NN (SDNN) data. In some embodiments, calculating HRV comprises analyzing root mean square of the successive differences (RMSSD) data. In some embodiments, calculating HRV comprises analyzing a ratio of low-frequency power divided by high-frequency power (LH/HF ratio).

In some embodiments, the heart rate measurement and mental state detection method further comprises adding the neutral time event marker to a particular time segment of the heart rate data timeline spanning a video timeline segment spanning a first video timeline position at a moment of completion of a first activity and a second video timeline position at a moment of starting performance of a second activity.

In some embodiments, the heart rate measurement and mental state detection method further comprises visually outputting a pop-up box through which the user viewing the time-synchronized heart rate data and video can evaluate the outcome of the performance of the activity and mark the performance of the activity with an activity performance outcome designation. In some embodiments, the activity performance outcome designation is selected by the user from a plurality of activity performance outcome designations. In some embodiments, the plurality of activity performance outcome designations comprise a good performance designation, a regular performance designation, a mistake designation, and a nothing designation. In some embodiments, the activity performance outcome designation is entered as free-form text input by the user.

In some embodiments, the heart rate measurement and mental state detection method further comprises visually outputting a report writing interface tool which, when selected by the user, generates a report of the performance of the activity with respect to one or more calculated parameters comprising the HRV data, the HRD data, the HRA data, the SDNN data, the RMSSD data, and the LH/HF ratio.

As stated above, the existing sports and fitness devices and apps can measure athletic performance (such as speed, strength, etc.), other body states, and vitals in real time, but fail to provide any measurable aspect pertaining to attention, focused attention, direction of attention, mental states, etc. Currently, however, there is technology to record reliable data to validate heart rate deceleration to measure the direction of attention which predicts better performance.

Nevertheless, none of the existing devices/apps utilize heart rate deceleration and/or heart rate acceleration as a measure of focused attention (if directed in the right direction) in the realm of athletics performance and performance of other activities. Embodiments of the heart rate measurement and mental state detection system and method described in this specification solve such problems by using heart rate deceleration and heart rate acceleration, among several other measurable parameters related to heart interbeat interval data, as measures of an athlete's emotional or mental state during a pre-action phase and in real-time as the athlete is about to start the activity or performance. Specifically, the heart rate measurement and mental state detection system and method are configured to measure mental states of individuals engaged in an activity, such as an athletic performance, and explain the outcome of the activity/athletic performance based on the measured/detected mental states. To do this, the heart rate measurement and mental state detection system captures images/video of activities/athletic performances. In addition, the heart rate measurement and mental state detection system pairs the captured images/video with other systems and algorithms that are implemented in software and validated in the field of sport psychophysiology to measure the heart inter beat interval (IBI), which is used to calculate and determine if Heart Rate Deceleration (HRD) or Heart Rate Acceleration (HRA) occurred during the pre-action phase of the activity/athletic performance (especially in self-paced sports in which the individual chooses to perform action when ready). Looking at the last thirty years of athletic training literature, HRD and HRA have been validated as a biomarkers (biological markers) of selective attention (also referred to in this specification as 'focused attention', 'focus', 'attention', 'attentional state', and like terms that relate to the manner in which an individual focuses his or her attention). Specifically, HRD occurs when the individual follows or focuses on a target and either when planning an action towards the target, such as planning to shoot a free throw in basketball through a basketball hoop, or when anticipating movement by or from the target, such as observing swelling of ocean water forming a wave and anticipating how the wave will break by a surfer or a body boarder. Thus, HDR has been validated as a biomarker indicating focused attention in the external stimulus (external attention or focus).

On the other hand, HRA has been validated as a biomarker indicating focused attention in internal stimuli (internal attention or focus), such as sensations of the body or internal thoughts (which may be calming or, on the contrary, anxiety inducing or nervous thoughts). For example, high levels of arousal (above what is needed for the action at hand) can decrease the person's ability to control attention. Worries about the outcome of performance (anxiety) can be characterized by the occurrence of HRA instead of HRD. Yet, HRA can occur at times when the internal attention actually improves performance by the athlete, which can be determined by evaluation of other heart rate parameters derived from the heart rate data, in combination and slightly before noted occurrences of HRA. At a high level, these HRD, HRA, and other heart rate parameter metrics are evaluated by first recording the heart interbeat interval (IBI) during athletic performance (including at least the pre-action and action phases). Videos of athletic performances are also captured and the interbeat interval is paired with the captured videos of athletic performances. From such analyzing of the recorded athletic performance and analyzing the heart rate data, instantaneous feedback on an athlete's emotional state during performance is possible. In this way, the heart rate measurement and mental state detection system pro-vides an effective way to improve the mental preparation of athletes and evaluate the efficiency of current mental train-ing programs. When the heart rate measurement and mental state detection system is used over a long span of time—not just a one-time use of capturing video and heart rate data of a single athletic performance, but over an entire season, for example—the amount of data from which it is possible to evaluate outcomes is staggering. That is, enough video and corresponding heart rate data is accumulated (e.g., over an entire season) so that a comparison of an athlete at the start of the season with the same athlete at the end of the season (or any other point within the season) is possible. In this way, a coach and player can see when the athlete was performing his or her best and worst (and everything in between) and personalize training programs that seem to bring out the best performance for the athlete. In some other scenarios, however, athletes and/or coaches are interested in very specific moments arising in a single performance of an activity (that is, not over an entire season). The heart rate measurement and mental state detection system of the present disclosure is highly suited for this purpose since it is configured to inform coaches and athletes of the individual's response during critical moments of competition or engage-ment in the activity. Similarly, third parties (not athletes themselves or even their coaches) may benefit from the analysis and outcomes determined by the heart rate mea-surement and mental state detection system. Specifically, sports commentators may be better informed about an athlete's actual attentional/emotional states for a given per-formance, which could inadvertently lower the incidence of prejudicial comments that devalue athletes (e.g., changing the narrative from "the athlete does not care anymore so performance is lacking" to "the athlete seems to be stuck on prior failures which impacts the athlete's ability to focus attention on the activity at hand"). Among many other benefits, the heart rate measurement and mental state detec-tion system also provides insights for others. For instance, one may use other short and long-term Heart Rate Variability (HRV) analyses during real-time performance in connection with the heart rate measurement and mental state detection system to inform trainers about athletes' physical and mental wellness.

Embodiments of the heart rate measurement and mental state detection system described in this specification differ from and improve upon currently existing options. In par-ticular, the existing devices and fitness apps are limited to merely recording a person's heart rate (e.g., 60 beats per minute). In contrast, the heart rate measurement and mental state detection system of the present specification involves HRV analysis (heart rate recorded in milliseconds) and pairing it with simultaneous performance to give instanta-neous feedback to coaches. This also involves analysis and detection of (i) HRD (in milliseconds) during the seconds prior to action as a measure of focused attention and (ii) HRA (in milliseconds) during the seconds prior to action (the prior action period being approximately six seconds before the action is performed) as indicative of the athlete having intrusive thoughts (worries and overthinking) prior to action. This prior action period (or "pre-action phase") is critical to actual performance of the activity.

Up to now, HRD and HRA have only been used in research. None of the existing apps and no one else has ever developed a system that uses the technology existent in cardiology (measuring the heart interbeat interval/ECG) and exercise physiology (determining the proper dosage of exer-cise) to improve the mental preparation of athletes. Yet, that is precisely what the heart rate measurement and mental state detection system of the present disclosure is designed to use. In this way, the heart rate measurement and mental state detection system is the only (and the first) technology used in competitive sport to inform coaches, athletes, and fans about the psychophysiological states of athletes during real-time performance. Imagine beyond sports and athlet-ics—the heart rate measurement and mental state detection system could be deployed at other professions that require focused attention on the task at hand prior to action. Before the heart rate measurement and mental state detection sys-tem, the prior systems, apps, and techniques for evaluating psychological states during the performance were measured only by questionnaires administered after the athletic per-formance, which makes conclusions unreliable. Further-more, the questionnaires were typically answered by the athletes themselves, which—as a subjective vector of data—also may be unreliable. Thus, while the heart rate measure-ment and mental state detection system described in the present specification provides immediate benefits to the work of athletes and sport psychology professionals, the data collected by the heart rate measurement and mental state detection system will generate new questions, theories, and hypotheses to be tested in many health and human performance sciences.

Prior to the heart rate measurement and mental state detection system, no one ever developed a device that can measure if the athlete is directing attention in the right way (internal focus versus external focus), to the right thing, and at the right time and give feedback to coaches and athletes right after the performance. For example, if a tennis player is preparing to receive a serve, and the person gets stuck in negative thinking during the six seconds that precede ath-letic performance, HRA (indicating internal focus on obtru-sive thoughts) instead of HRD (indicating focus on reading the external stimulus such as the opponent movements) will occur. On the other hand, a gymnast performing on a routine on a balance beam would preferably show HRA as a predictor of better performance since performing athletically on the beam requires focus on internal sensations of the body instead of external stimulus.

Up to now, the technology to record reliable data during sport performance was not sufficient for validating HRD, HRA, and other heart rate data-related parameters, as mea-sures of performance or mental state. Consequently, no one ever developed a device that can measure if the athlete is paying attention to the right thing at the right time and give feedback to coaches and athletes right after the performance. For example, if a tennis player is preparing to receive a serve, and the person gets stuck in negative thinking during the six seconds that precede athletic performance, HRA (indicating internal focus on obtrusive thoughts) instead of HRD (indicating focus on reading the external stimulus such as the opponent movements) will occur. On the other hand, a gymnast performing on a routine on a balance beam would show HRA as a predictor of better performance since performing athletically on the beam requires focus on inter-nal sensations of the body instead of external stimulus. While tennis player and gymnast have different attentional processes at play, both would benefit from a system that is able to give instantaneous feedback about their attention or mental state. Today this is possible since there is technology available to record reliable data to register the occurrence of HRD and HRA as measures of focused attention that predict better performance. As such, the heart rate measurement and mental state detection system can provide more accurate predictions with respect to performance and also provide feedback and explanation to coaches/athletes about their ability in comparison with their highly attuned (appropriate) focused attention or their lack focused attention during the critical moments of competition.

The heart rate measurement and mental state detection system of the present disclosure may be comprised of the following elements or components. This list of possible constituent elements/components is intended to be exemplary only and it is not intended that this list be used to limit the heart rate measurement and mental state detection system of the present application to just these elements/components. Persons having ordinary skill in the art relevant to the present disclosure may understand there to be equivalent elements and components that may be substituted within the present disclosure without changing the essential function or operation of the heart rate measurement and mental state detection system.

1. An electronic and sensor-based device that measures the heart interbeat interval (in milliseconds). In some embodiments, a heart rate monitor (or sensor) is such a device which, when worn around a chest area of an individual, captures heart rate data as the individual engages in an activity (including the pre-action and action phases of the activity). Other sensor-based devices are also supported, as described below, but a heart rate monitor/sensor is preferred. In some embodiments, a smart watch is used in connection with the heart rate monitor. In some embodiments, the smart watch itself is configured to act as a heart rate monitor.

2. A camera, such as a video camera (or camcorder), a camera of a device (e.g., a GoPro camera, an embedded camera of a mobile device, etc.), a camera of an aerial drone, a camera of a water vessel drone, a DSRL camera capable of capturing still frame images and video, a mirrorless camera capable of capturing still frame image and video, etc. The camera captures a sequence of images of the activity being performed. The sequence of images may be in the format of frames of a video (e.g., thirty frames per second recording, sixty frames per second recording, etc.) or separate frames captured by the camera with time-spacing between each captured image (still-frame images, photographs, pictures, etc.).

3. Software that is configured to perform the heart rate variability analysis and can show several different heart rate parameters that help the individual to determine how they performed during the activity. The several different heart rate parameters include at least heart rate deceleration (HRD), heart rate acceleration (HRA), standard deviation of NN (SDNN), root mean square of the successive differences (RMSSD), and a ratio of low-frequency power divided by high-frequency power (LH/HF ratio).

4. A computing device on which the software runs and which is configured to visually output the video/imagery and heart rate data (as analyzed) in a time-synchronized playback view that enables the individual (and any coach or specialist helping the individual) to evaluate the hard data in connection with particular moments while engaging in the activity.

The various elements and components of the heart rate measurement and mental state detection system of the present disclosure may be related in the following exemplary fashion. It is not intended to limit the scope or nature of the relationships between the various elements and the following examples are presented as illustrative examples only. The heart rate monitor is a chest-strap type of heart rate monitor that is wrapped around an individual's torso so that the sensor embedded in the heart rate monitor chest strap is positioned approximately around the chest/heart area. The heart rate monitor may include an embedded wireless device that is configured to dump the heart rate data into a connected/paired smart watch (e.g., worn by the individual and, there, close in proximity to the heart rate monitor and, thus, allowing for simple Bluetooth pairing). Alternatively, the heart rate monitor may be integrated into the smartwatch and provide the same function as a chest-strap type of heart rate monitor. Typically, a smartwatch capable of capturing the relevant heart rate data is a high-end smartwatch with a sensor that is highly sensitive to heart rate and is able to differentiate heart rate from other noise (e.g., the smartwatch is not the average heart rate monitor that is found in cheap sport watches). The data is transmitted to the computing device if and when the heart rate monitor and/or the smartwatch is equipped with a low power, long range wireless data transmitter, such as an ANT+ RF device or a Gymlink communications device. Such RF communications device is also supported for water-based activities, in which Bluetooth communications may not be supported (as Bluetooth is not configured to operate under water). The computing device (e.g., a laptop, a tablet, a PC, etc.) is operated by a user, such as a coach, a sport psycho-physiologist, an athlete friend of the individual performing the activity, or any sport psychology practitioner who knows how to interpret the data. The software combines the athletic performance imagery/video with the heart rate data from the heart rate monitor. The software is able to evaluate the data in real-time (as it is received) and determine relevant aspects of the individual's mental state ("direction of attentional", "attentional direction", or "attentional state"). For instance, if HRD is detected during the pre-action phase just before action of the individual for the activity, this bodes well for body boarding, surfing, and many other activities in which attention/focus is best when externalized. On the other hand, some athletes, such as gymnasts performing a routine on the balance beam, may perform better if and when HRA is detected in the pre-action phase. There is a caveat in this respect: HRA may signify arousal, such as would be brought on by nervousness and anxiety before performance of the activity, and this typically would predict a worse performance outcome than if HRD is detected. Yet, the attentional focus needed in some scenarios (such as walking the balance beam and performing other highly skilled actions on the beam) is optimized for the athlete if and when the focus is internalized (not externalized). When a person's focus is internalized, HRA is a detected. To determine when an instance of HRA is actually beneficial, one may evaluate the heart rate data further to derive SSNN data. If SSNN is detected approximately three seconds before the action (and, thus, before the pre-action phase), then HRA detected in the pre-action phase indicates that the athlete's internal focus pertained to balance and bodily aspects involved in balance. Clearly, this suggests the importance of review by a sport psychophysiologist or sport psychology professional or practitioner. For instance, a sport psychophysiologist or sport psychology practitioner can tell if heart rate deceleration occurred due to the metabolic demands of the sport or as a result of focused attention prior to performance. The sport psychology practitioner would enter feedback into the system (at the computing device) or would send the feedback to the individual (e.g., email, text, etc.). In less than a minute after an athletic performance in self-paced sports, the athlete can receive feedback about his/her mental/emotional state and self-regulate.

In some embodiments, the heart rate measurement and mental state detection system can be equipped with or provide other wearable devices (in lieu of, or in combination with, the heart rate monitor/sensor) which an individual dons before engaging in the activity at hand. In some embodiments, the heart rate measurement and mental state detection system comprises an electroencephalography cap that is worn by the individual and is configured to capture EEG data of the individual and measure brain activity that demonstrate changes in direction of selective attention, in real-time, during performance of the activity by the individual. In some embodiments, the heart rate measurement and mental state detection system comprises an EEG sensor headband device comprising an EEG sensor embedded in a headband worn by the individual and configured to capture EEG data and measure brain activity in real-time during performance of the activity. Nevertheless, the heart rate monitor is utilized in a preferred embodiment of the heart rate measurement and mental state detection system since electroencephalography is highly sensitive to movement artifacts. Furthermore, athletes are more likely to wrap a heart rate monitor around their torso than an electroencephalography cap since many athletes may feel or sense that they look awkward wearing a cap full of wires. This, in and of itself, can distract the athlete in a way the gives rise to occurrences of HRA, when the athlete really needs to have focused attention, demonstrated by occurrence of HRD (or likewise, depending on the demands of the activity). In addition to the above, an electroencephalography cap is not preferred by every sport has rules related to external equipment brought to be used during the athletic performance, and a heart rate monitor is more discrete and can be fitted under a shirt. Finally, heart rate monitor readings are less polluted by motion artifacts and can be worn without disrupting the athlete's performance or even being seen.

The heart rate measurement and mental state detection system and method of the present disclosure generally works by understanding that the mind and the body are really one-a single inseparable entity. Therefore, it is possible to know what is happening in the person's mind by analyzing heart rate (cardiac activity is related to psychological phenomena is multiple studies back to 1960s, 1970s, and 1980s). Of course, the heart rate monitor is not the average heart rate monitor found in many sports watches. The software quantifying the data must be able to artifact the data, match it to a video, and calculate if heart rate deceleration occurred. The person watching the data must know how to interpret it. Because there are multiple movements in preparation for sport performance, the individual (sport psychology professional) must identify if there is a pause in the seconds before action and decide if the data reflects the measurement of focused attention. Then the data is sent back to the athlete through the watch. For example, the feedback during a tennis match or an entire surfing competition can be used to develop better mental training interventions to help athletes calm themselves during the critical moments of competition.

To make the heart rate measurement and mental state detection system and method of the present disclosure, software should implement functions and procedures to interpret the data captured and aggregated in real time. The data should be time coded in coordination with the video of the performance. In the hardware device would be at least a high-quality heart rate monitor, video capture (can be separated) to record instantaneous video of athletic performance, and the software to add images and data and quantify the data, app on the smartphone to give feedback, etc. Other embodiments can deploy different sensors or hardware. For instance, instead of a heart rate monitor, one may utilize an electroencephalogram recorder (EEG). To date, there are no electroencephalogram recorders resistant to movement artifacts. Heart rate monitors in belts transmitting the signal to the smartphone or transmitting the signal straight to the computer software can also be used. Eye movement tracking devices could also be an option in some embodiments of the heart rate measurement and mental state detection system. Similarly, devices capable of capturing physiological data from electromyography (EMG) could be deployed for use with the heart rate measurement and mental state detection system.

To use the heart rate measurement and mental state detection system and method of the present disclosure, feedback given to the athlete and/or coaches can be used to measure and improve the mental preparation of athletes. Outside users or interested parties may also use this. For example, sports commentators can obtain fast (nearly real-time) feedback on what is going on inside the athlete's heads (emotional and mental states) instead of just making guesses based on facial looks, expressions, etc., or just randomly to entertain spectators. If heart rate deceleration occurs and the athlete performs poorly, it indicates technical flaws that are not visible to the coach and not a problem with athlete's mental preparation. This is the type of information and feedback that was impossible previously. An example of how to use the heart rate measurement and mental state detection system is described next, by reference to FIG. 1.

By way of example, FIG. 1 conceptually illustrates a heart rate measurement and mental state detection method for measuring heart interbeat interval and detecting a direction of attention of an individual ("the athlete") engaged in an activity. As shown in this figure, the heart rate measurement and mental state detection method starts with the athlete wearing the heart rate monitor (or heart rate sensor) around their chest. Once applied to the athlete, the heart rate monitor collects heart rate data (also referred to as "R-R interval" data in this example). The heart rate monitor itself may be equipped with a wireless communications module, such as Bluetooth, ANT+, or Gymlink. In some scenarios, such as when the athlete is engaged in a water sport, ANT+ or Gymlink are preferred for wireless communications since Bluetooth does not support data communications when submerged in water. Similarly, when the athlete is positioned too far from the laptop computer (or tablet computing device), ANT+ is preferred for wireless communications since Bluetooth only supports data transmissions over a smaller distance than ANT+.

Returning to the heart rate measurement and mental state detection method shown in FIG. 1, other software and algorithms that are validated in the scientific field are implemented into the system software and are used to analyze the heart rate data captured by the heart rate monitor. The system software (or "app") is wirelessly connected or connected via wired connection (via cable) to a video camcorder or other camera configured to capture video and able to transmit video out to a computing device. The app is also capable of downloading or retrieving the heart rate data (when not wirelessly transmitted by the heart rate monitor) and/or downloading/retrieving the video data captured by the video camcorder.

As shown at the next step of the heart rate measurement and mental state detection method, the app pairs simultaneous data from the video recorder (that video stream data or imagery data) and the heart rate monitor/sensor (the heart rate data or R-R interval data). Next, event markers are added to the data that is being collected as the video is watched. The event markers include pre-action, action, sport demand, neutral time, no go, downtime, and custom event markers. These event markers delimit the full time into time segments that can be calculated using heart rate variability analysis of HRD, HRA, SDNN, RMSSD, and LH/HF ratio. In some embodiments, the interpretation of data requires a specialist in sport psychophysiology and one who understands the demands of the activity at hand (e.g., the sport or action being recorded). Users can interact by marking "neutral time" after every clip of an athletic performance or performance of an activity. Similarly, the user will be prompted by a pop-up box where it is possible to evaluate the outcome of performance, such as good performance, regular performance, under performance, mistake, and nothing, among other optional outcome designations. Finally, the heart rate measurement and mental state detection method provides for report generation. In some embodiments, reports can be generated by the user selecting (clicking) a calculate tool in combination with a particular parameter the user wishes the report to focus on. This is the basic manner of how one goes about using the heart rate measurement and mental state detection system.

Now, turning to another example, FIG. 2 conceptually illustrates a heart rate measurement and mental state detection system that configured to capture a video of an individual engaging in an activity and capture heart rate data of the individual to instantaneously detect and measure focused attention of the individual during a pre-action phase and as the individual performs the activity. As shown in this figure, the individual is a surfer 10. A video recording device 14 is communicably connected to a laptop computer 15. When the surfer 10 is wearing the heart rate monitor (wrapped around the torso/chest of the surfer 10), the heart rate data captured by the heart rate monitor is provided to the laptop computer 15. The laptop computer 15 has the software installed. When the software is running on the laptop computer 15, the video stream captured by the video recording device 14 is provided to the laptop computer 15 and visually output 16 in a media player interface 22 of the software (and shown on a screen of the laptop computer 15). The heart rate data received from the heart rate monitor is time-synchronized to a timeline of the video stream, such that after the software analyzes the heart rate data, a viewer can compare the analyzed and validated heart rate data to the video stream and pinpoint particular timeline moments where HRD and/ or HRA occurrences arose for the surfer 10.

In some embodiments, the heart rate measurement and mental state detection system is deployed for use with a laptop computer and a tablet computing device or, alternately, with a tablet computing device but no laptop computer. In the next examples, described below by reference to FIGS. 3-4, such alternate configurations are shown.

Specifically, FIG. 3 conceptually illustrates components of an alternate configuration of a heart rate measurement and mental state detection system with the video recording device 14, the laptop computer 15, and a tablet computing device 17 deployed for use.

Now turning to another variation, FIG. 4 conceptually illustrates components of a limited alternate configuration of a heart rate measurement and mental state detection system with only the video recording device 14 and the tablet computing device 17 while a user is operating the tablet computing device 17.

While the heart rate measurement and mental state detection system described above, by reference to FIG. 2, demonstrated a media player interface 22 of the software and visual output 16 of the video stream captured and provided by the video recording device 14, the heart rate data captured by the heart rate monitor worn by the surfer 10 was not shown. This is described next, by reference to FIG. 5, which conceptually illustrates an example view of a heart rate data analysis and validation view 20 with formatted heart rate data as provided for review along a timeline that is synchronized to the video timeline of the video stream visually output 16 in the media player interface 22 of the software on the screen of the laptop computer 15. If, instead of the laptop computer 15, the tablet computing device 17 is deployed for use, the same heart rate data analysis and validation view 20 with formatted heart rate data would be visually output onto a screen of the tablet computing device 17.

Now, turning to another example, FIG. 6 conceptually illustrates a selective controls and event markers panel 24 and a custom signal panel 12 of an interface of the software. Specifically, the selective controls and event markers panel 24 allows a user to select from several controls to add event markers to the heart rate data, calculate heart rate data parameters (including HRD, HRA, SDNN, RMSSD, and LH/HF), and perform artifact correction (e.g., average, ignore, and report). The custom signal panel 12 includes a graph with a PQRS heart wave (signal) which helps a sport psychophysiologist to see artifacts and correct them. The area under the custom signal panel 12 also shows heart rate monitor data 18.

In another example, FIG. 7 conceptually illustrates a combined view of the selective controls and event markers panel 24, the custom signal panel 12 with the PQRS heart wave (signal) graph, the heart rate monitor data 18, the media player interface 22 of the software which allows a viewer to start video playback of the captured video, and the heart rate data analysis and validation view 20 with formatted heart rate data as provided for review along a timeline that is synchronized to the video timeline of the captured video shown in the media player interface 22.

Additionally, the heart rate measurement and mental state detection system and method of the present disclosure gives performance feedback and can be used not only to improve the training of athletes but also to improve the performance of surgeons, police officers, and military special forces. It can be used in any technology that needs a measurement of focused attention. Also, the heart rate measurement and mental state detection system and method can be adapted and used in products or devices that want to measure attention (without the athletic performance aspect). For instance, during tasks requiring selective attention and strategic planning (even while sitting), a heart rate deceleration occurs during the seconds prior to action.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on electronic systems, define one or more specific machine implementations that execute and perform the operations of the software programs.

By way of example, FIG. 8 conceptually illustrates an electronic system 30 with which some embodiments of the invention are implemented. The electronic system 30 may be a computer (a laptop computer, a personal computer (PC), a desktop computer, a single board computer (SBC), a server computer, etc.), a mobile device/phone (cell phone, mobile phone, smartphone, etc.), a tablet computing device, a personal digital assistant (PDA) device, or any other sort of electronic device or computing device. Such an electronic system includes various types of computer readable media and interfaces for various other types of computer readable media. Electronic system 30 includes a bus 32, processing unit(s) 34, a system memory 36, a read-only memory 38, a permanent storage device 40, input devices 42, output devices 44, and a network 46.

The bus 32 collectively represents all system, peripheral, and chipset buses that communicatively connect the numerous internal devices of the electronic system 30. For instance, the bus 32 communicatively connects the processing unit(s) 34 with the read-only memory 38, the system memory 36, and the permanent storage device 40.

From these various memory units, the processing unit(s) 34 retrieves instructions to execute and data to process in order to execute the processes of the invention. The processing unit(s) may be a single processor or a multi-core processor in different embodiments.

The read-only-memory (ROM) 38 stores static data and instructions that are needed by the processing unit(s) 34 and other modules of the electronic system. The permanent storage device 40, on the other hand, is a read-and-write memory device. This device is a non-volatile memory unit that stores instructions and data even when the electronic system 30 is off. Some embodiments of the invention use a mass-storage device (such as a magnetic or optical disk and its corresponding disk drive) as the permanent storage device 40.

Other embodiments use a removable storage device (such as a floppy disk or a flash drive) as the permanent storage device 40. Like the permanent storage device 40, the system memory 36 is a read-and-write memory device. However, unlike storage device 40, the system memory 36 is a volatile read-and-write memory, such as a random access memory. The system memory 36 stores some of the instructions and data that the processor needs at runtime. In some embodiments, the invention's processes are stored in the system memory 36, the permanent storage device 40, and/or the read-only memory 38. For example, the various memory units include instructions for processing the raw heart rate data received from the heart rate monitor or smart watch, analyzing and validating the heart rate data, and preparing formatted graphical visual output of the validated heart rate data, as well as performing time synchronization of heart rate data with video received from the camera, and other runtime processing as required to provide enhanced information for athletes and coaches seeking to identify HRD and/or HRA occurrences and build or revise a training regimen that maximizes the athlete's focused attention on the task at hand, whatever sport or activity is being performed. From these various memory units, the processing unit(s) 34 retrieves instructions to execute and data to process in order to execute the processes of some embodiments.

The bus 32 also connects to the input and output devices 42 and 44. The input devices enable the user to communicate information and select commands (e.g., adding event markers, calculating heart rate data parameters, generating reports, etc.) to the electronic system. The input devices 42 include alphanumeric keyboards and pointing devices (also called "cursor control devices"). The output devices 44 display analyzed and validated heart rate data and associated graphical data, as well as video captured by the camera and/or images captured by the camera and rendered by the electronic system 30. The output devices 44 include printers and display devices, such as cathode ray tubes (CRT), liquid crystal displays (LCD), and organic light emitting diode (OLED) displays. Some embodiments include devices such as a touchscreen that functions as both input and output devices.

Finally, as shown in FIG. 3, bus 32 also couples electronic system 30 to a network 46 through a network adapter (not shown). In this manner, the computer can be a part of a network of computers (such as a local area network ("LAN"), a wide area network ("WAN"), or an intranet), or a network of networks (such as the Internet). Any or all components of electronic system 30 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIG. 1 conceptually illustrates a process in which the specific operations of the process may not be performed in the exact order shown and described.

Specific operations may not be performed in one continuous series of operations, and different specific operations may be performed in different embodiments. Furthermore, the process could be implemented using several sub-processes, or as part of a larger macro process. Thus, one of ordinary skill in the art would understand that the invention is not to be limited by the foregoing illustrative details, but rather is to be defined by the appended claims.

I claim:

1. A heart rate measurement and mental state detection system comprising:

a computing device comprising a processing unit, a storage device, and a screen, wherein the computing device is located in a first area;

a heart rate monitor comprising a wireless communication module and which is wearable by an individual during a span of time associated with performance of an activity by the individual in a second area that is a distance away and different from the first area, wherein the heart rate monitor is communicably connected remotely from the second area to the computing device located in the first area during the span of time associated with performance of the activity, wherein performance of the activity comprises a physical act by the individual in the second area, wherein the span of time comprises a pre-action phase of up to six seconds before the individual engages in the physical act and an action phase that starts at a moment in the span of time when the individual engages in the physical act, wherein the heart rate monitor is configured to (i) capture heart rate data of the individual during the pre-action phase and the action phase while the individual performs the activity in the second area over the span of time and (ii) provide, to the computing device in the first area, the heart rate data in real-time and in sequence as the heart rate data is being captured, wherein the computing device stores the heart rate data provided by the heart rate monitor in the storage device;

a camera that is communicably connected locally to the computing device located in the first area and is configured to (i) capture, contemporaneously with the heart rate monitor capturing the heart rate data of the individual, imagery of the individual during the pre-action phase and the action phase while the individual performs the activity in the second area over the span of time and (ii) transmit the imagery to the computing device in sequence as the imagery is being captured, wherein the computing device stores the imagery transmitted by the camera in the storage device; and a sport heart rate monitoring software application that is installed on the computing device, stored on the memory device, and which, when running on the processing unit of the computing device located in the first area, is configured to (i) receive the heart rate data in sequence along a heart rate data timeline comprising the pre-action phase and the action phase, (ii) locally receive the imagery in sequence along a video timeline comprising the pre-action phase and the action phase, (iii) synchronize the video timeline of the imagery with the heart rate data timeline of the heart rate data, (iv) utilize a scientifically validated algorithm to perform heart rate variability (HRV) analysis of the heart rate data associated with the pre-action phase of the heart rate data timeline, (v) visually output, onto the screen of the computing device, the timeline-synchronized heart rate data and imagery, (vi) visually output, onto a pre-action time segment of the timeline-synchronized heart rate data and imagery visually output onto the screen of the computing device, a pre-action event marker based on the HRV analysis associated with the pre-action phase of the heart rate data timeline, and (vii) generate a report of an outcome based on the HRV analysis of the heart rate data associated with the pre-action phase of the heart rate timeline after performance of the activity is completed.

2. The heart rate measurement and mental state detection system of claim 1, wherein the camera comprises a video camera that is configured to capture a video of the individual performing the activity, wherein the video of the individual performing the activity comprises a sequence of video frames corresponding to the sequence of imagery transmitted to the computing device, wherein the video timeline comprises a plurality of time segments, wherein the plurality of time segments comprises the pre-action time segment and an action time segment.

3. The heart rate measurement and mental state detection system of claim 1 further comprising a smart watch that is worn by the individual in the second area and is paired to the heart rate monitor, wherein the smart watch comprises a wireless Bluetooth watch module that is configured to send and receive data wirelessly to and from the wireless communication module of the heart rate monitor.

4. The heart rate measurement and mental state detection system of claim 3, wherein the wireless communication module of the heart rate monitor comprises a wireless Bluetooth communications module that is configured to pair to the wireless Bluetooth watch module of the smart watch and further configured to simultaneously send the heart rate data wirelessly to the smart watch while providing the heart rate data to the computing device in the first area, wherein the sport heart rate monitoring software application is further configured to generate and transmit, back to the smart watch worn by the individual in the second area, data indicating that the heart rate data reflects a measurement of focused attention during performance of the activity.

5. The heart rate measurement and mental state detection system of claim 1, wherein the sport heart rate monitoring software application is further configured to detect heart rate deceleration (HRD) during the pre-action phase.

6. The heart rate measurement and mental state detection system of claim 1, wherein the sport heart rate monitoring software application is further configured to detect heart rate acceleration (HRA) during the pre-action phase.

7. The heart rate measurement and mental state detection system of claim 1, wherein the heart rate monitor comprises a wireless radio-frequency (RF) device that is configured to send and receive wireless data to and from the computing device.

8. The heart rate measurement and mental state detection system of claim 7, wherein the RF device comprises an ANT+ wireless communications device that is configured to send the heart rate data to the computing device in real-time as the heart rate data is captured by the heart rate monitor.

9. A heart rate measurement and mental state detection method for measuring heart interbeat interval and detecting a direction of attention of an individual engaged in an activity, said heart rate measurement and mental state detection method comprising:

applying a heart rate monitor approximately to a body area of an individual, wherein the heart rate monitor comprises a wireless communication module;

starting, on a computing device located in a first area that is different from a second area in which the individual performs an activity involving focused attention, a sport heart rate monitoring software application that is installed on the computing device;

connecting, by way of one of a wireless connection and a wired connection, a camera located in the first area to the computing device located in the first area;

providing a wireless connection between the wireless communication module of the heart rate monitor, when the individual is in the second area, and the computing device located in the first area, wherein the wireless connection enables remote access, by the sport heart rate monitoring software application on the computing device located in the first area, to heart rate data of the individual performing the activity involving focused attention in the second area;

simultaneously starting, at a simultaneous start time, the heart rate monitor and the camera, wherein the heart rate monitor captures and transmits, to the sport heart rate monitoring software application on the computing device located in the first area, a sequence of heart rate data of the individual while the individual performs the activity involving focused attention in the second area, wherein the camera captures a sequence of images (video) of the individual while the individual performs the activity involving focused attention in the second area, wherein performance of the activity spans a duration of time comprising a pre-action time period corresponding to a pre-action phase during which the individual prepares to perform the activity and an action time period corresponding to an action phase during which the individual actively performs the activity;

capturing, by the heart rate monitor, heart rate data during both the pre-action phase as the individual prepares to perform the activity and the action phase as the individual actively performs the activity;

wirelessly transmitting in real-time, to the sport heart rate monitoring software application of the computing device by the wireless communication module of the heart rate monitor, the captured heart rate data during both the pre-action phase as the individual prepares to perform the activity and the action phase as the individual actively performs the activity;

receiving, by the sport heart rate monitoring software application of the computing device in real-time, the sequence of heart rate data captured by the heart rate monitor and transmitted by the wireless communication module, wherein the sequence of heart rate data corresponds to a heart rate data timeline;

analyzing and validating, by the sport heart rate monitoring software application of the computing device, the received heart rate data;

capturing, by the camera in the first area and simultaneously with the heart rate monitor capturing the heart rate data of the individual in the second area, the sequences of images as a video of the individual during both the pre-action phase as the individual prepares to perform the activity and the action phase as the individual actively performs the activity;

receiving, from the camera and by the computing device in real-time as the camera captures the sequences of images, a video stream of the video captured by the camera, wherein the video stream is received as a plurality of sequential video frames corresponding to a video timeline;

pairing, by the sport heart rate monitoring software application during performance of the activity by the individual in the second area, the sequence of heart rate data along the heart rate data timeline with the plurality of sequential video frames of the video stream along the video timeline;

synchronizing, by the sport heart rate monitoring software application, the heart rate data timeline of the sequence of heart rate data with the video timeline of the video stream of the video starting at the simultaneous start time ("synchronized timeline"), wherein the video timeline comprises a plurality of video time segments corresponding to the plurality of sequential video frames of the video stream, wherein the heart rate data timeline comprises a plurality of heart rate data time segments corresponding to the plurality of video time segments;

visually outputting, on a screen of the computing device by the sport heart rate monitoring software application, the time-synchronized video and heart rate data for playback viewing by a user operating the computing device in the first area during performance of the activity by the individual in the second area;

adding event markers to the heart rate data as the video is being viewed by the user during playback, wherein the event markers delimit the pre-action phase as a first time segment of the plurality of video time segments and the corresponding plurality of heart rate data time segments from the action phase as a second time segment of the plurality of video time segments and the corresponding plurality of heart rate data time segments; and calculating heart rate variability (HRV) data based on changes in the heart rate data between the first time segment and the second time segment, wherein calculating HRV comprises at least one of (i) detecting heart rate deceleration (HRD) during the pre-action phase, (ii) detecting heart rate acceleration (HRA) during the pre-action phase, (iii) detecting standard deviation of NN (SDNN), (iv) detecting root mean square of the successive differences (RMSSD), and (v) detecting a ratio of low-frequency power divided by high-frequency power (LH/HF ratio).

10. The heart rate measurement and mental state detection method of claim 9, wherein adding the event markers to the heart rate data as the video is being viewed by the user during playback comprises adding a neutral time event marker to delimit a particular time segment that does not overlap the pre-action phase and the action phase of the synchronized timeline, wherein the particular time segment is different from the first time segment and the second time segment, wherein the neutral time event marker added to the synchronized timeline spans a plurality of timeline positions along the synchronized timeline from a first timeline position at a moment of completion the action phase of a first activity and a second timeline position at a moment of the pre-action phase upon starting performance of a second activity.

11. The heart rate measurement and mental state detection method of claim 10, wherein adding the event markers to the heart rate data as the video is being viewed by the user during playback further comprises adding one or more of a pre-action event marker, an action event marker, a sport demand event marker, a no go event marker, a downtime event marker, and a custom event marker.

* * * * *